(12) United States Patent
Loxley et al.

(10) Patent No.: US 10,820,878 B2
(45) Date of Patent: Nov. 3, 2020

(54) APPARATUS AND METHOD FOR THE CORRECTION OF SCATTER IN A RADIOGRAPHIC SYSTEM

(71) Applicant: IBEX INNOVATIONS LIMITED, Sedgefield (GB)

(72) Inventors: Neil Loxley, Sedgefield (GB); Paul Scott, Sedgefield (GB)

(73) Assignee: IBEX INNOVATIONS LIMITED, Sedgefield (GB)

(*) Notice: Subject to any disclaimer, the term of this patent is extended or adjusted under 35 U.S.C. 154(b) by 0 days.

(21) Appl. No.: 16/489,978

(22) PCT Filed: Mar. 1, 2018

(86) PCT No.: PCT/GB2018/050528
§ 371 (c)(1),
(2) Date: Aug. 29, 2019

(87) PCT Pub. No.: WO2018/158577
PCT Pub. Date: Sep. 7, 2018

(65) Prior Publication Data
US 2020/0237333 A1  Jul. 30, 2020

(30) Foreign Application Priority Data

Mar. 1, 2017 (GB) .................................. 1703291.3

(51) Int. Cl.
*A61B 6/00* (2006.01)
*G06T 11/00* (2006.01)
(52) U.S. Cl.
CPC .......... *A61B 6/5282* (2013.01); *A61B 6/4233* (2013.01); *A61B 6/4291* (2013.01);
(Continued)
(58) Field of Classification Search
USPC .......................................... 382/128, 131–132
See application file for complete search history.

(56) References Cited

U.S. PATENT DOCUMENTS

| 5,440,647 | A | 8/1995 | Floyd, Jr. et al. |
| 7,308,072 | B2 * | 12/2007 | Ruhrnschopf ......... A61B 6/032 378/7 |

(Continued)

FOREIGN PATENT DOCUMENTS

| WO | 2009/136400 A2 | 11/2009 |
| WO | 2016/051212 A1 | 4/2016 |

OTHER PUBLICATIONS

International Search Report & Written issued in corresponding application No. GB1803343.1, dated Aug. 31, 2018, 3 pgs.

(Continued)

*Primary Examiner* — Ishrat I Sherali
(74) *Attorney, Agent, or Firm* — Meunier Carlin & Curfman LLC

(57) ABSTRACT

An x-ray imaging method comprises the steps of: providing a set of at least one training material, the set comprising different materials and/or different thicknesses of the or each material; obtaining observed x-ray images of the at least one training material with a pixellated detector; building a database in a simulator of simulated scatter kernels for variable parameters within the simulator for each of the at least one training material; generating a transfer function between parameters of the simulator and parameters of the observed image which is independent of sample type and thickness; generating a whole image scatter estimate; predicting the direct radiation for each scatter kernel; applying the transfer function to the scatter estimate and the direct radiation or the inverse of the transfer function to the observed intensity values; performing the calculation Z–S–D<threshold to provide scatter free data and/or a scatter free image.

11 Claims, 11 Drawing Sheets

(52) U.S. Cl.
CPC ............ *A61B 6/482* (2013.01); *A61B 6/5205* (2013.01); *A61B 6/583* (2013.01); *G06T 11/005* (2013.01); *G06T 2207/10116* (2013.01)

(56) References Cited

U.S. PATENT DOCUMENTS

| | | | |
|---|---|---|---|
| 10,588,592 B2* | 3/2020 | Scott | A61B 6/5282 |
| 10,631,815 B2* | 4/2020 | Rui | G01N 23/046 |
| 2008/0095313 A1* | 4/2008 | Ruhrnschopf | A61B 6/482 |
| | | | 378/98.4 |
| 2010/0046696 A1* | 2/2010 | Maltz | G06T 11/005 |
| | | | 378/7 |
| 2013/0259344 A1 | 10/2013 | Petersilka et al. | |
| 2015/0342554 A1* | 12/2015 | Mentrup | A61B 6/582 |
| | | | 378/154 |
| 2015/0371414 A1 | 12/2015 | Choi et al. | |
| 2016/0086328 A1 | 3/2016 | Enomoto et al. | |
| 2018/0146935 A1* | 5/2018 | Song | A61B 6/4014 |

OTHER PUBLICATIONS

International Search Report and Written Opinion, issued by the International Searching Authority (ISA/EP) in PCT Application No. PCT/GB2018/050528 dated Jun. 26, 2018. 11 pages.

* cited by examiner

APPARATUS AND METHOD FOR THE CORRECTION OF SCATTER IN A RADIOGRAPHIC SYSTEM

FIELD OF THE INVENTION

The present invention relates to an apparatus and method for the correction of scatter in a radiographic system, and in particular to such an apparatus and method in which an anti-scatter grid is not used.

BACKGROUND OF THE INVENTION

When an object is subjected to x-ray radiation some of the x-ray photons are absorbed and some pass through the object, unscattered, to impinge on an x-ray detector. This is referred to as "direct radiation". Some x-rays are absorbed and others are scattered. The intensity of the scatter produced may exceed the magnitude of the direct radiation detected by the detector. The scattered radiation results in poor image quality by reducing contrast and increasing noise. Absorbed x-rays provide the contrast in an x-ray image. If scattered x-ray photons hit the detector random noise in the image is increased since it is not possible to identify where the scattered x-ray photons have come from.

The most widely adopted technique used to address the problem of scatter is to place an anti-scatter grid between the x-ray detector and the object under test. An anti-scatter grid comprises a series of spaced apart parallel lamellae formed of x-ray absorbing material. A large proportion of scattered x-rays engages one of the lamella and is absorbed. It is therefore predominantly the direct radiation that is detected by the x-ray detector when an anti-scatter grid is present.

The original anti-scatter grid is described in U.S. Pat. No. 1,164,987 (Bucky).

One of the problems with anti-scatter grids is that in addition to reducing the effect of scatter in the detected image, the x-ray absorbing lamellae absorb some of the direct radiation, that is those photons travelling in the path of the lamellae.

In order compensate for the photons lost in the anti-scatter grid and hence the reduced image quality, it is common practice to increase the x-ray flux. However, this is disadvantageous where the x-ray imaging is of x-ray sensitive material. This is of most concern in medical imaging where the x-ray radiation dose to the patient must be increased to compensate for the presence of the anti-scatter grid.

Some attempts have been made to reduce the x-ray power used in x-ray imaging.

U.S. Pat. No. 7,551,716 instead of using an anti-scatter grid uses mathematical methods to determine approximately the scatter x-ray photons. It is asserted that by utilising mathematical methods to determine approximately the scatter x-ray photons, the x-ray dose can be reduced or the signal to noise ratio increased when compared with an x-ray apparatus using an anti-scatter grid. The mathematical method used in U.S. Pat. No. 7,551,716 relies on making an assumption about the material under investigation, that being that the tissue is mammary tissue and that the tissue has a certain thickness as a result of compression of the tissue between compression paddles.

An x-ray apparatus that includes a multi-absorption plate is described in the applicant's patent application published under number GB2498615. In this x-ray apparatus the x-ray energy spectrum is perturbed in many different ways. This apparatus and method provides information that allows material properties to be identified.

The applicant's patent application published under number WO2016/051212 describes an apparatus which imposes a change on the x-ray signal that affects both the direct and scattered radiation and which allows scatter radiation be identified and in some embodiments for the identified scatter radiation to be added back as if it were direct radiation.

Whilst the invention described in WO2016/051212 allows x-ray dose to be reduced and signal to noise ratio to be improved, the structure that is used to impose a change on the x-ray signal nevertheless absorbs x-ray radiation.

It would be desirable to provide an apparatus and method which provides the advantages of the apparatus and method described in WO2016/051212 but which allows the x-ray dose to be reduced still further and/or for the signal to noise ratio to be improved.

As well as providing for measurement of scatter radiation, the present invention provides for the measurement of scattered radiation to be used in the identification of materials and thicknesses of materials and in improving the contrast to noise ratio.

By establishing a transfer function between an observed x-ray image and a simulation of an x-ray image that is material and thickness invariant, information from the observed and simulated images becomes interchangeable, subject to application of the transfer function. It is possible to separate direct and scatter radiation in the simulation. Scatter radiation can therefore be removed from the observed image. It is thereby possible to increase the contrast to noise ratio. In the context of medical applications and other applications where x-rays are used to analyse materials that may be harmed by x-rays, the present invention allows either the dose to be reduced to produce a similar standard of image, or using the same x-ray dose a better image can be generated.

SUMMARY OF THE INVENTION

According to the invention there is provided an x-ray imaging method comprising the steps of:
 i. providing a set of at least one training material, the set comprising different materials and/or different thicknesses of the or each material;
 ii. obtaining observed x-ray images of the at least one training material with a pixellated detector;
 iii. building a database in a simulator of simulated scatter kernels for variable parameters within the simulator for each of the at least one training material;
 iv. comparing parameters of the observed image and parameters of the image created by the simulator and identifying input parameters to the simulator which give rise to a transfer function between the identified input parameters of the simulator and the parameters of the observed image which is independent of sample type and thickness.
 v. generating the transfer function;
 vi. obtaining an observed x-ray image with the pixellated detector of a sample that contains at least one material resembling the at least one training material;
 vii. making an initial estimate of the material type and/or thickness contained in the sample;
 viii. performing a ray path trace on the sample as if the material and thickness of the sample corresponds to the estimate of step viii from each of a plurality of spatially separated points on the sample to each pixel of the detector;
 ix. obtaining a scatter kernel from a scatter kernel database corresponding to a spread function of the ray path trace;
 x. sum the scatter for each scatter kernel to provide a whole image scatter estimate;

xi. predict the direct radiation for each scatter kernel;

xii. apply the transfer function to the scatter estimate and the direct radiation or the inverse of the transfer function to the observed intensity values;

xiii. perform the calculation Z–S–D<threshold where Z is the observed intensity value, S is the scatter radiation post application of the transfer function and D is the direct radiation post application of the transfer function;

xiv. if Z–S–D<threshold subtract S from Z to provide scatter free data and/or a scatter free image.

Preferably, the database of scatter kernels built in step iii is built for a sub-set of all variable parameters within the simulator for each of the at least one training material.

The variable parameters in step iii may be selected from the group comprising: kV, filtration and sample position.

Advantageously, the step of obtaining an x-ray image with a pixellated detector comprises recording intensity values at each pixel of the detector.

The initial estimate (step viii) may be based on one of: the intensity values associated with individual pixels or groups of pixels from step vii; a statistical value related to the materials and material thicknesses contained in the database of training materials; a random guess; material type and thickness information from another system.

It is preferred that, obtaining a scatter kernel database comprises one of: emulating a scatter kernel from scatter kernels in the scatter kernel database; interpolating between scatter kernels from the scatter kernel database; and selecting a scatter kernel.

The scatter kernel database may be sparsely populated and scatter kernels are emulated from or interpolated between points in the sparsely populated scatter kernel database.

The x-ray imaging method may include the further step of adding back to the scatter free data, scatter radiation as if that scatter radiation had been direct radiation and providing enhanced scatter free data and/or an enhanced scatter free image.

The scatter free data may comprise material type and/or material thickness information.

Preferred features of the method are also set out in the description and drawings of this specification.

According to a second aspect of the invention there is provided an x-ray imaging apparatus comprising an x-ray source, a pixellated x-ray detector, a simulator and a data processor, the data processor configured to perform at least the steps ii to v of the x-ray imaging method of the first aspect of the invention.

The data processor may be configured to perform at least the steps vi to xiv of the x-ray imaging method of the first aspect the invention.

According to a third aspect of the invention there is provided an x-ray imaging apparatus comprising an x-ray source, a pixellated x-ray detector, a simulator and a data processor, the data processor configured to perform at least the steps vi to xiv of the x-ray imaging method of the first aspect of the invention.

Preferred features of the apparatus are also set out in the description and drawings of this specification.

According to a fourth aspect of the invention there is provided an x-ray imaging system x-ray imaging system comprising x-ray imaging apparatus of the second or third embodiments of the invention and a set of at least one training material, the set comprising different materials and/or different thicknesses of the or each material.

The method, apparatus and system of the invention do not require an anti-scatter grid to remove scatter from x-ray imaging data. Removal of scatter is achieved by the method of the first aspect of the invention. Further, the method does not require a measurement of sample thickness to be taken.

BRIEF DESCRIPTION OF THE DRAWINGS

In the Drawings, which illustrate preferred embodiments of the invention, and are by way of example.

DETAILED DESCRIPTION OF THE PREFERRED EMBODIMENTS

Figure 1A:
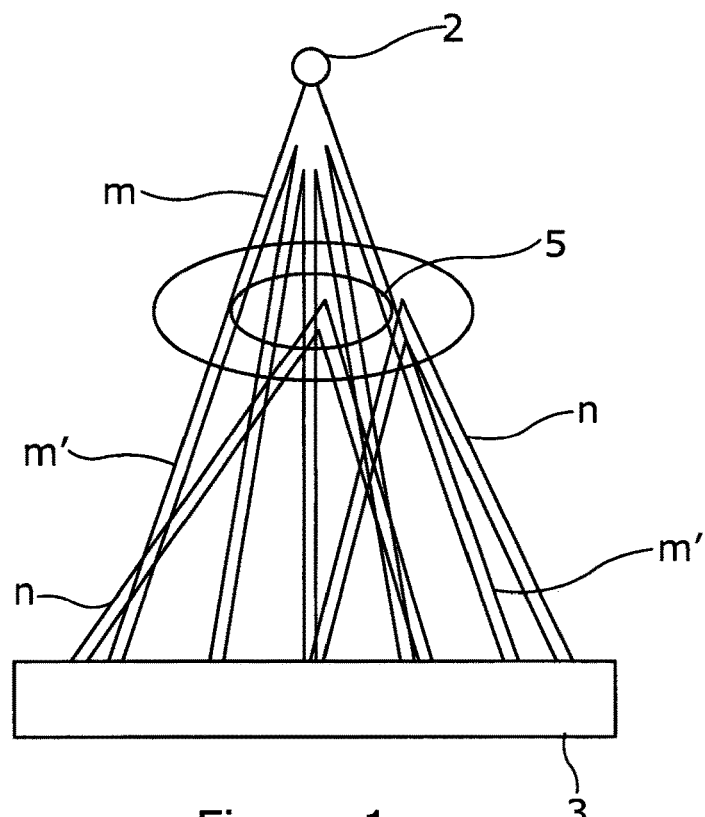
FIGS. 1a and 1b illustrate an embodiment of apparatus of the invention.
Figure 1B:
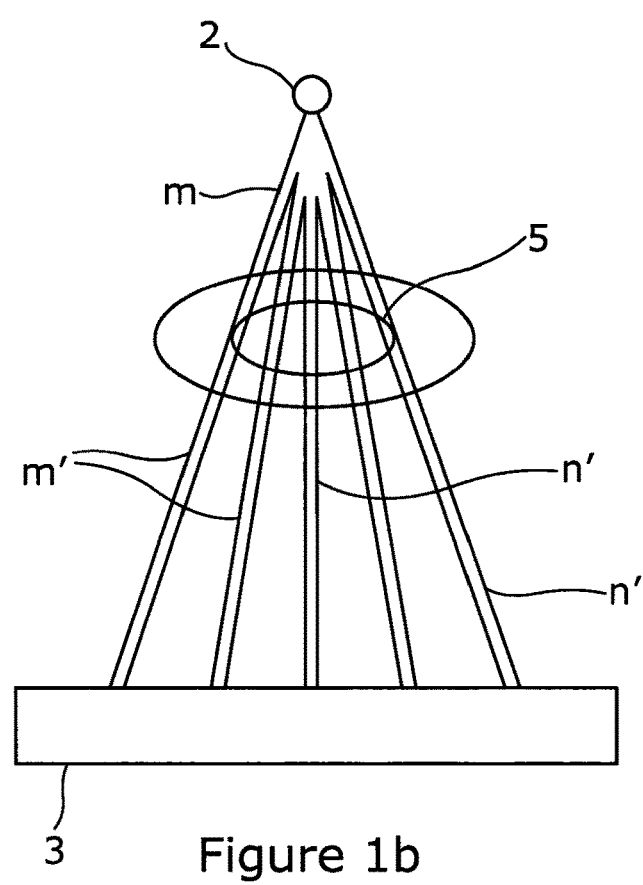

FIGS. 1a and 1b, show an apparatus 1 according to an embodiment of the invention. An x-ray source 2 is aligned with a detector 3.

FIG. 1a illustrates what happens to x-ray photons that are incident on a material under test 5. Of the x-ray photons m emitted from the x-ray source 2, some of the x-ray photons m' pass straight through the material under test 5 to impinge on the detector 3, these x-ray photons representing "direct radiation", some are absorbed and some x-ray photons n are scattered.

The scatter x-ray photons n are undesirable. This embodiment of the invention allows the scattered x-ray photons n shown in FIG. 1a to be removed from the image and re-assigned as pseudo-direct radiation n' to the direct radiation m' with which they were associated. The result is that, as illustrated in FIG. 1b, the output of any one pixel of the detector 3 resulting from x-ray photons impinging thereon comprises the direct radiation m' and the re-assigned pseudo-direct radiation n'. This increases the contrast and hence the contrast to noise ratio in the image generated by the detector 3, and also provides a more desirable image because the scattered x-ray photons n are not removed as would be the case with an anti-scatter grid, but are added to the output signal at a spatial location of the detector that the x-ray photons would have interacted with had they not been scattered. The result is therefore to boost the image contrast.

Even without the step of reassignment of scatter the contrast and contrast to noise ratio are improved.

The method of the invention, which provides for the removal the scatter photons n from the detected image and where preferred the re-assignment of scatter photons as pseudo-direct radiation n' comprises first and second components. In the first component a database of values is created, those values being related to materials which resemble materials that might be analysed in the second component.

The hypothesis underlying the present invention is that when simulating the effect of x-ray photons on a particular material, group of materials and different thicknesses of material or materials, if such a simulation and an observed x-ray image have the same underlying spectrum of energies, then the simulation can be used as a representation of the observed x-ray image and any processing done using information from the simulator will be useful as if it were from the observed x-ray image.

The advantage of using data from a simulation rather than data from an observed x-ray image is that in a simulator it is possible to separate scatter radiation from direct radiation.

First Component of the Method—Creating a Transfer Function

A group of training materials is selected. The training materials may be the materials that would be encountered in a proposed use of the apparatus and method of the invention or they may be materials that have a very similar effect on x-ray photons to the materials with which the apparatus and method of the invention would be used.

An observed x-ray dataset is obtained from the detector 3 for the selected training materials for various thicknesses thereof. For example, an x-ray dataset for each of five different thicknesses of PMMA and five different thicknesses of aluminium may be obtained.

A database of the scatter patterns of different materials and different thicknesses thereof is created in a simulator for a subset of all parameters in the simulator that are variable for the selected training materials (for example but not limited to—a range of kVs, sample positions, a range of air gaps, a range of filtration). In an embodiment where the x-ray apparatus is to be used for imaging body parts then polymer polymethyl methacrylate (PPMA) and aluminium might be used as being representative of how x-ray photons are affected by flesh and bone respectively.

The output of each pixel of the detector 3, or the output of groups of pixels of the detector 3 (for the parameter that corresponds to the subset of parameters simulated, for example kVs) is compared with the database of scatter patterns for the subset of parameters in order to arrive at a transfer function that, within the bounds of random error, does not vary with material type or thickness of material. That is, there may be a difference between the output of a particular pixel or a particular group of pixels of the detector 3 and the scatter pattern that most closely matches the output of the pixel or group of pixels, but that difference is a multiplier and does not change with material type or material thickness. Hence, where the closest match for the selected parameter between the data from the observed x-ray and the data from the simulator is an exact match then the transfer function would be 1. In another case where closest match for the selected parameter between the data from the observed x-ray and the data from the simulator requires the value of the selected parameter from the simulation to be multiplied by 2, then the transfer function is 2.

In the first component of the method the algorithm iterates for each pixel or group of pixels possible transfer functions until a match (within random error) between one or more parameters of the data from the x-ray detector and the same one or more parameters of the data from the simulation is reached.

It should be noted that even where the material is uniform in type and thickness, the transfer function deduced for one pixel or group of pixels may be different to the transfer function deduced for an adjacent pixel or group of pixels. It is desirable to deduce the transfer function pixel by pixel or group of pixels by group of pixels in order to take account of Heal effects arising from the x-ray source. Obviously, if the group of pixels comprises all the pixels of the detector then the transfer function will be common to all pixels.

Second Component of the Method—Generating a Scatter Corrected Image of a New Sample Pre-Capture Calibration The method may include a pre-capture calibration of the x-ray source and detector involving the collection of bright field and dark field images.

Image Capture and Preprocessing

An x-ray image (Z) of the scattering object is captured by the pixellated detector 3.

The captured image is calibrated for example for dark and bright field correction.

A sub-sample of the image may be taken. This step may aid computational efficiency.

Scatter Estimation

Step 1: The first step in estimating scatter is to make an initial estimate of the material type and thickness of the scattering object based on the x-ray image (Z). The basis of this estimate may depend on the type of equipment in which the apparatus and method of the invention is deployed. For instance, the initial estimate may be based on the intensity values for individual pixels or groups of pixels, a statistical value related to the materials and material thicknesses containing in the database of training materials, or the initial estimate may however be a random guess.

Figure 6:
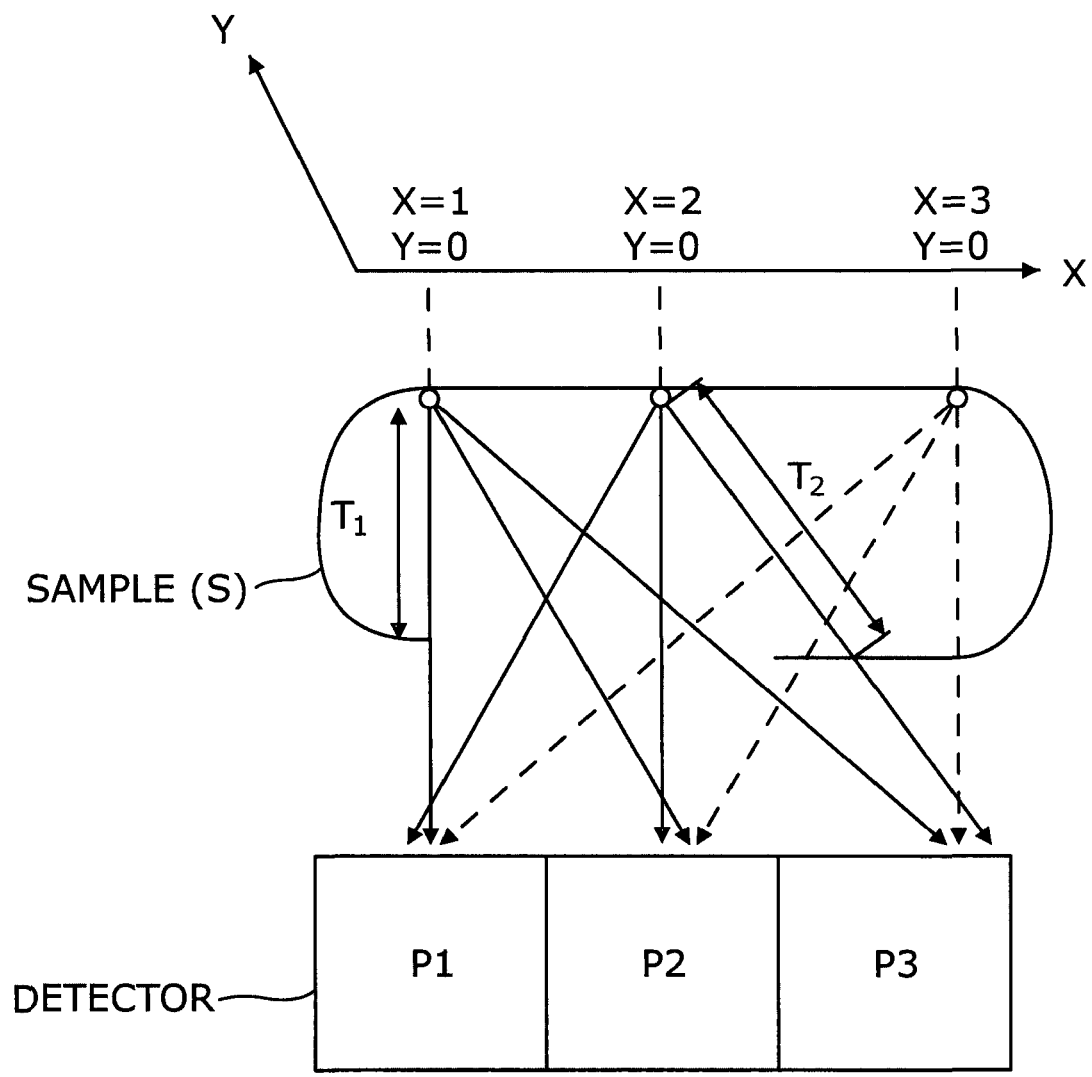
FIG. 6 illustrates ray path tracing between the sample and the detector.

Step 2: The second step is to perform a ray path trace of each ray emanating from each one of a selected number of points on the entrance face of the sample (the sample assumed to be of the estimated material type and thickness) to every pixel or group of pixels within the image. This is illustrated in FIG. 6. This ray path trace allows an indication of the material type and thickness that x-ray photons would have passed through (if the observed material type and thickness were the same as the estimated material type and thickness) to be developed.

As can be seen from FIG. 6, an x-ray photon following path x=1, y=0 to P1 passes through material of thickness T1, whereas an x-ray photon following the ray path extending from x−2, y=0 to pixel 3 (P3) passes through a material having a thickness T2.

Step 3: The third step comprises obtaining a scatter kernel that corresponds as closely as possible to the estimated material type and thickness and spread function for each ray path. One way of obtaining the scatter kernel is by emulating the estimated material type and thickness and spread function for each ray path from points in a sparsely populated scatter kernel database. Alternatively, the ray trace could be compared with a very large database of scatter kernels and the closest match selected.

Step 4: The fourth step comprises applying the transfer previously calculated for each pixel or group of pixels to the scatter and direct radiation estimated for each pixel or group of pixels so that the simulated values of scatter and direct radiation can be used in the equation Z approximates to S+D where Z is the total radiation, which is the sum of the direct radiation D and the scatter radiation S. Of course, instead of applying the transfer function to S and D, the inverse of the transfer function could be applied to Z. Ideally Z−S−D would equal zero. However, due to the random nature of components of an x-ray imaging system, which are well known to those skilled in the art, there will inevitably be a small difference between Z and S+D. Hence, in this specification we refer to Z−S−D<threshold and by this we mean that the threshold is not significantly different to the combination of tolerances introduced by the components of the x-ray imaging system.

The process of making simulated data correspond observed data is known as reification.

If the initial guess made in the first step above is the correct guess then Z−S−D<threshold.

Step 4a: This step is only completed if the result of Z−S−D is not 0, that is the initial estimate was not correct, which is likely. The first to fourth steps are iterated with a new initial guess in the first step on each iteration. The new initial estimate may be a new random guess, a statistical value not previously used or a material type and thickness estimate generated by another system.

Step 5: Once a satisfactory estimate of material type and thickness has been arrived at, that is Z−S−D<threshold the value of S for each pixel or group of pixels is subtracted from the value Z at each pixel of the detector 3. The result is a corrected scatter free image C.

Step 6: An optional step comprises adding back the scatter radiation to the scatter free image C, but as if the scatter radiation had not been scattered. This is described above in relation to FIGS. 1*a* and 1*b*.

Simulation Model

The simulation referred to above was carried out using a simulation model illustrated in FIG. 3, which simulates how different materials and different thickness thereof scatter when a pencil beam of x-ray photons are incident thereon.

By using a pencil beam that is aligned with one pixel of a multi-pixel detector, one can be certain that the x-ray photons reaching the pixel with which the source is aligned represent for the most part "direct radiation" or scattered radiation that has been scattered through a very small angle from the path of the direct radiation and that all x-ray photons detected by other pixels are scattered x-ray photons which came from the incident pencil beam. It is therefore possible to establish the signature scatter pattern of any material of a given thickness. By repeating this process for different thicknesses of the same materials, the signature patterns for different thicknesses of the same material can be established. Similarly, repeating the process for different materials and/or different thicknesses of those materials, a database of signature scatter patterns can be built up.

A Monte Carlo model of the x-ray system and x-ray physics was created using a software package called GEANT4 which simulates the passage of particles through matter. The model was used to simulate the result of a pencil beam of x-ray photons being incident upon different materials and thicknesses thereof. The results for different materials and different thickness thereof are recorded.

Figure 3A:
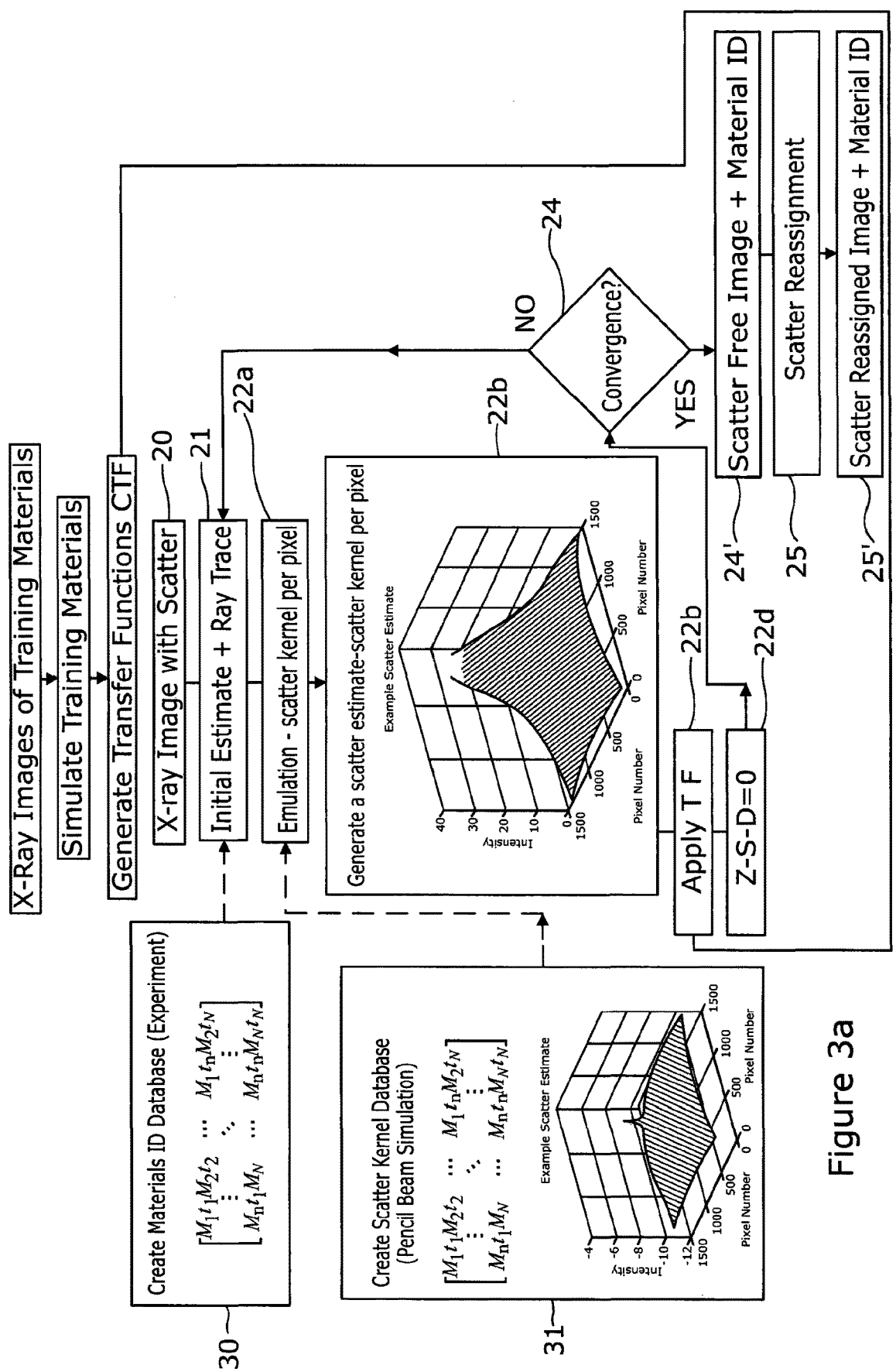
FIG. 3a is another flow chart illustrating the method of operation of the embodiment of the invention illustrated in FIGS. 1a and 1b.

Each scatter pattern has a shape similar to that shown in FIG. 3*a* in Graph 1. In relation to scatter, this is also known as a scatter kernel. For any one scatter kernel, the scattered photons represented by all the x-ray photons incident on pixels of the detector 3 that are not aligned with the pencil beam can be identified. Hence, the direct radiation and the scatter radiation in an image can be quantified. The scatter radiation may be removed from the image to provide an image of direct radiation only.

However, creating and using a database of signature scatter kernels for all materials of interest and their thickness would require vast data storage capacity and very powerful processing capability, or alternatively, using the data stored in such a database would be very slow.

The model of this embodiment of the invention therefore uses an interpolation technique in order to derive scatter kernels for combinations of materials and their thicknesses which have not themselves been specifically simulated. The technique of interpolation and in this embodiment emulation is not in itself new.

Figure 2:
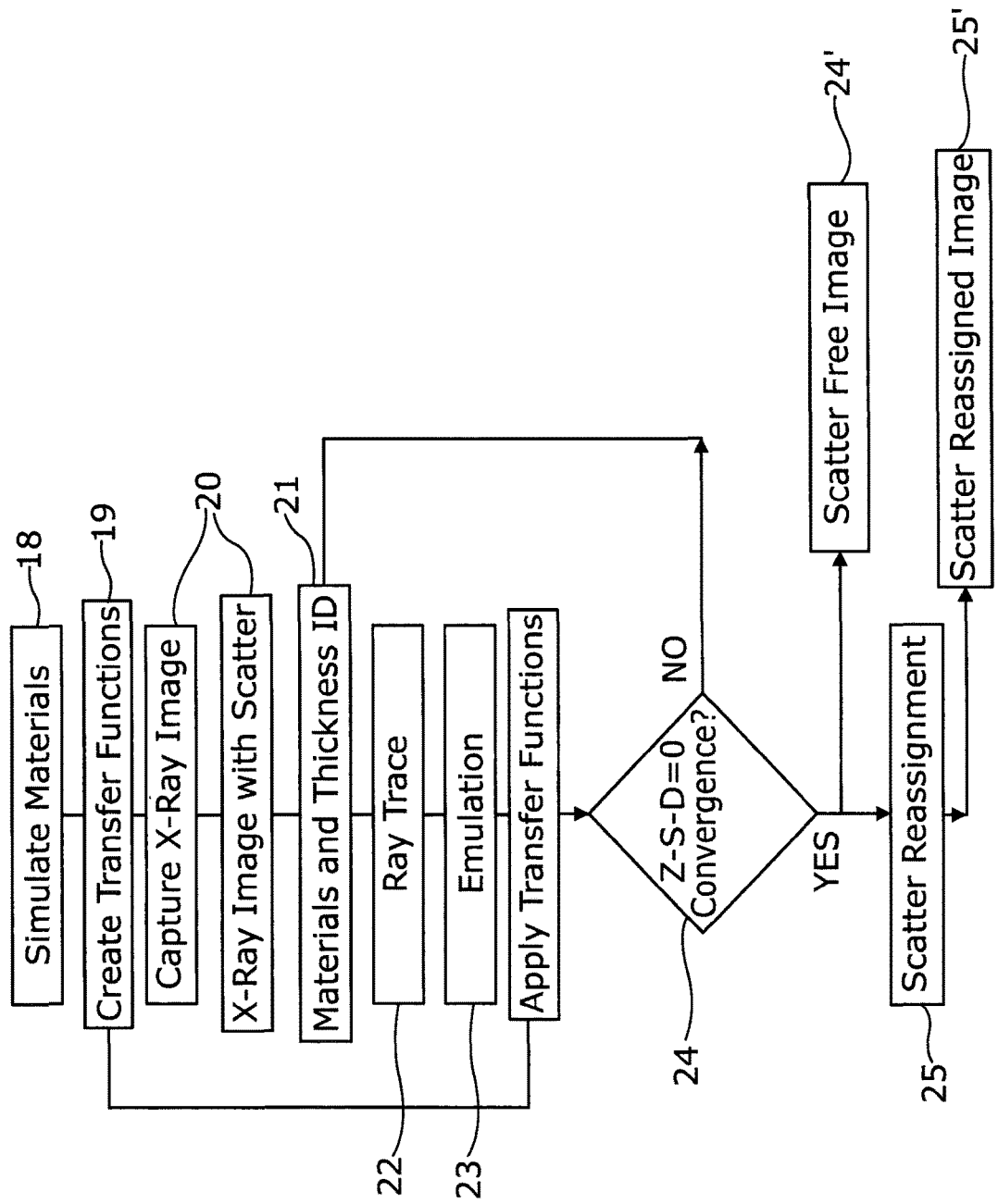
FIG. 2 is a flow chart illustrating the method of operation of the embodiment of the invention illustrated in FIGS. 1a and 1b.

FIG. 2 is a flow chart that shows how the process of the invention removes scattered x-ray photons from data recorded by the x-ray detector 3 to produce a scatter free image and/or an enhanced image where the scatter photons are re-assigned as pseudo direct radiation.

The flow chart illustrated in FIG. 3*a* illustrates the process shown in FIG. 2 in greater detail, in particular, the sub-steps of resulting in a scatter free image are illustrated.

In step 18 the effect of x-ray photons on training materials and different thicknesses thereof is simulated.

In step 19 a transfer function is created which is material and thickness invariant as between the simulated training materials and the effect of x-ray photons on an observed sample of the training materials.

In step 20 data for a new sample of materials that resemble the training materials is obtained, that date being in the form of energy intensities which are recorded by the detector 2, for each pixel thereof or group of pixels.

In step 21 a a first estimate of materials type and materials thickness is made. The term "material" includes combinations of materials. For example the output of this step may be that the material identified at a certain pixel of the detector 2 is muscle and bone. In fact, the output of this step 21 is a first estimate of the material identity and/or thickness. The first may be based on the darkness recorded at a pixel, may be a random guess or may be a statistical value related to information in a database 30. For example, the first guess may be the median of the material and thickness from the database of training materials. In the example described below the first guess was 5 cm of 50% PMMA/Aluminium.

Referring to FIG. 3*a* scatter kernels for the estimated materials are emulated in step 22*a*, that is from the database of scatter kernels 31, a scatter kernel is emulated (derived) for material estimated in step 21 for each pixel or group of pixels of the detector 2. The individual scatter kernels are convolved together in step 22*b*. This convolution of the scatter kernels forms what is known as the scatter estimate for the image, which is illustrated in Graph 2 in FIG. 3. As can be seen from Graph 2, there is a scatter value associated with each pixel of the detector in the scatter estimate. In step 22*c* the transfer function for the pixel or group of pixels for which the calculation is being performed is applied to the scatter estimate and the direct radiation for the scatter kernel convolved in step 22*b*. In step 22*d* the calculation Z−S−D<threshold is made. If Z−S−D<threshold then there is convergence and a scatter data set is created in step 24' and a scatter free image and/or material type and thickness identification may be created.

The step 25 of scatter re-assignment may be performed with or without the scatter free image and materials identification having been performed in step 24'. The output of step 22*c* is shown as a scatter free image 22*d*, which may be an image or may be intensity values from which may be represented as an image.

If the first guess at material and thickness in step 21 is incorrect, there will be no convergence at step 24 and the material and thickness first guess step 21 and subsequent steps will be repeated. This is done until Z–S–D<threshold in step 22d.

In step 24 a determination is made as to whether the scatter kernels match the scatter in the observed image, i.e. is Z–S–D<threshold. If the answer is NO, which it is likely to be for a number of iterations, steps 21 to 24 are iterated until the Z–S–D<threshold. If the answer is YES, the process moves on to step 25 where scatter is either re-assigned to produce an image with re-assigned scatter, or it is not re-assigned and a scatter free image is produced.

Values representative of materials identification and/or thickness may include contrast, scatter kernels, scatter estimates, etc.

With a reduced scatter effect, the materials identification in step 23 can produce a more accurate result, represented by a post convergence scatter free image 24'.

Steps 21 to 24 are reiterated until Z–S–D<threshold.

A scatter free image output may be taken after step 24 or the process may move on to step 25.

In step 25, where the output is an image with the scatter re-assigned by adding the removed scatter radiation to the output signal at a spatial location of the detector that the x-ray photons of the removed scatter radiation would have interacted with had they not been scattered. The result of the re-assignment step 25 is represented by a re-assigned image in step 25'.

Example 1

Scatter was removed from an image taken of a sample comprising a 7.6 cm block of PMMA with an insert of 1.36 cm of Aluminium.

X-ray imaging equipment comprising a GE medical system with 3 mm of aluminium filtration, an 80 kV, 5 mAs tungsten tube and a Rayence detector was used to obtain observed x-ray images.

A reification training set of materials representative of the sample comprised five 5 cm thick plates of PMMA and five 1 cm plates of aluminium.

Images of the training set of materials were taken using the x-ray imaging equipment in the following manner.

For PMMA a first x-ray image was obtained for the sample comprising one 5 cm thick PMMA plate of the training set. Second, third, fourth and fifth images were taken, each time adding one more 5 cm thick PMMA plate of the training set.

For aluminium a first x-ray image was obtained for the sample comprising one 1 cm thick aluminium plate of the training set. Second, third, fourth and fifth images were taken, each time adding one more 1 cm thick aluminium plate of the training set.

Figure 4:
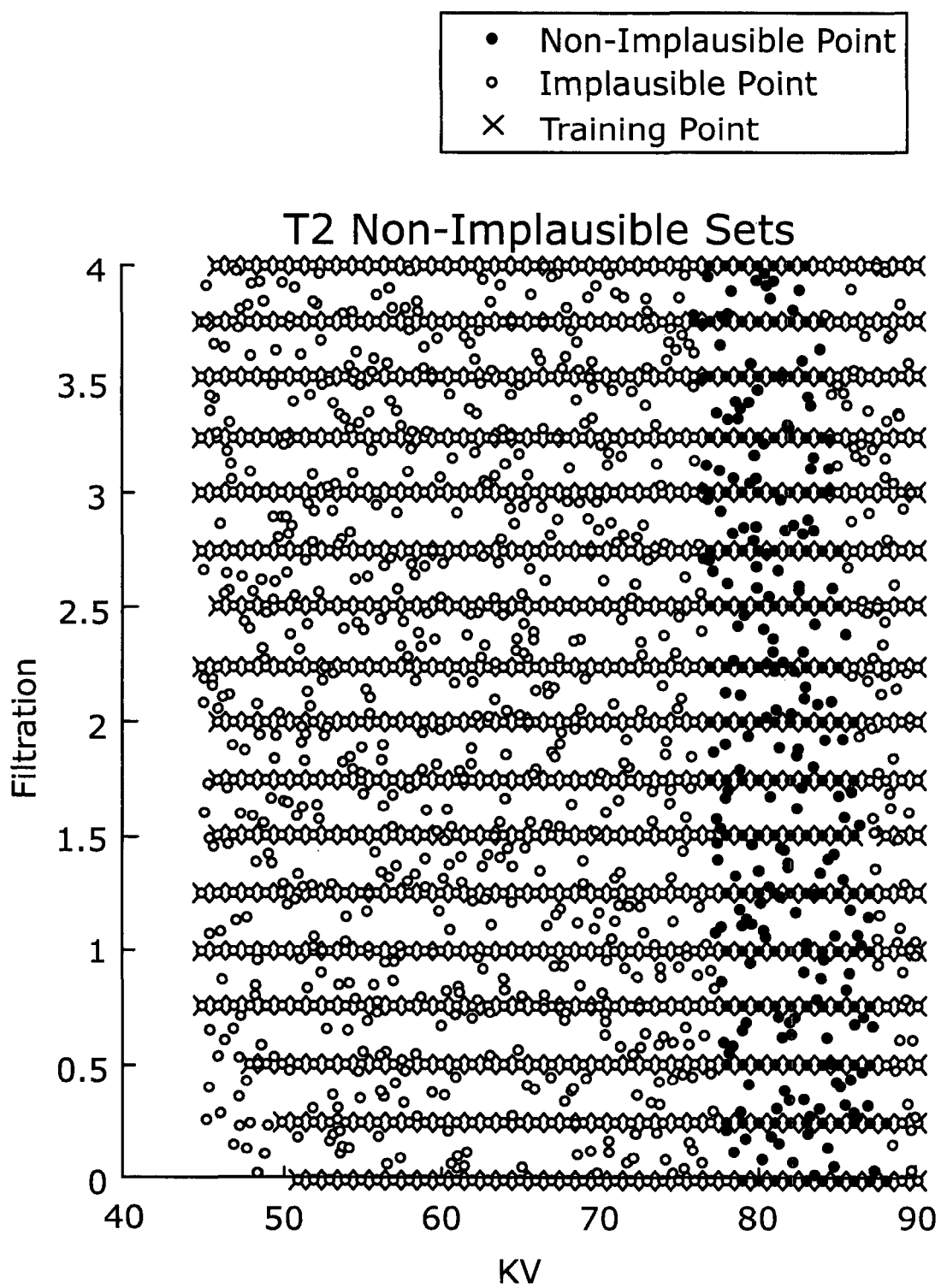
FIG. 4 is graph illustrating Non-Implausible settings for filtration v kV.
Figure 5:
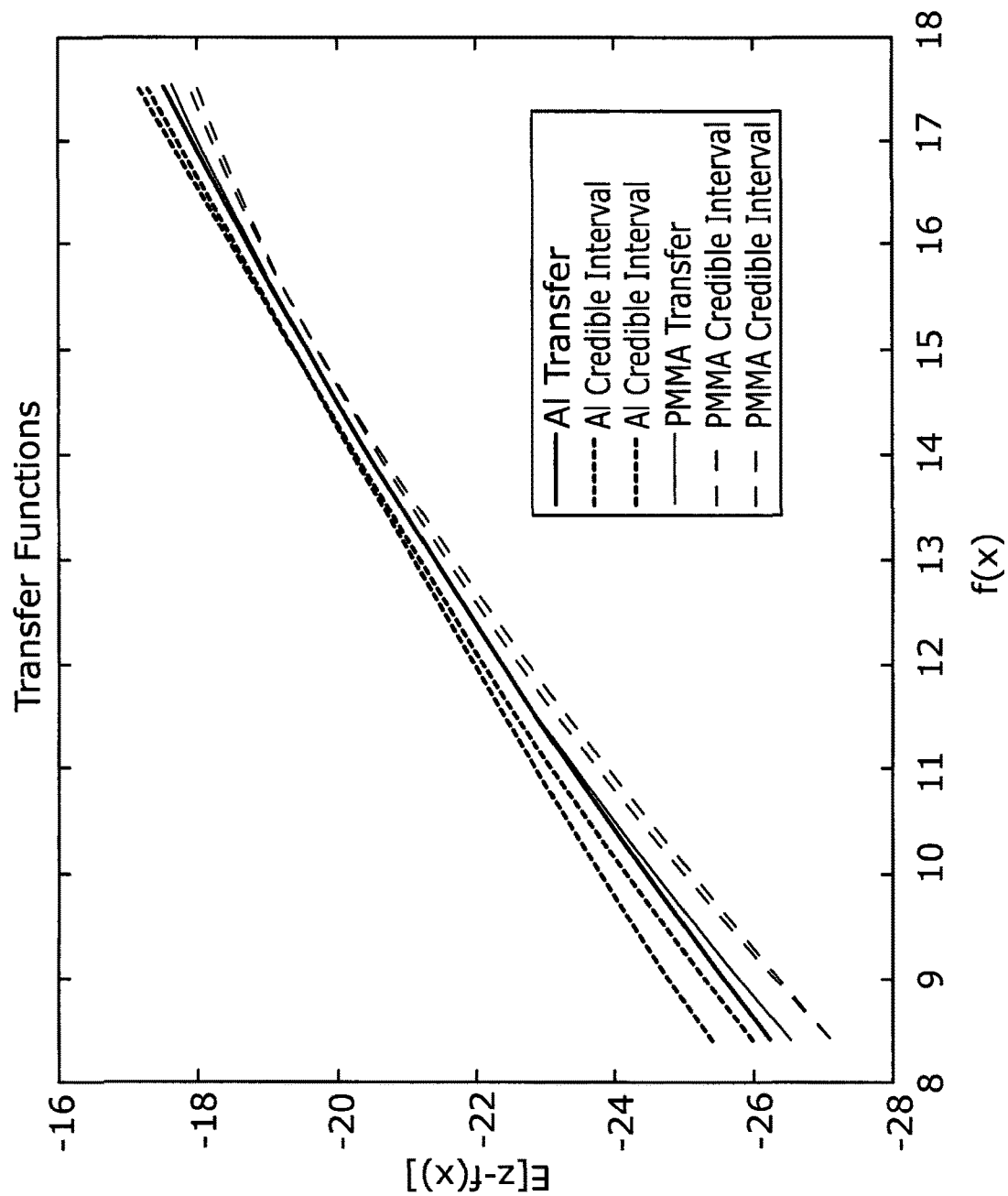
FIG. 5 is a graph of Transfer Functions for Aluminium and PMMA.

The "Offline" process describe above was followed. Simulator settings of 1.5 mm filtration and 76 kV produced a material and thickness invariant transfer function. See FIG. 4 and FIG. 5. With the simulator set at 1.5 mm filtration and 76 kV a spatially variant transfer field, that is a set of spatially variant transfer functions, was generated for individual pixels of the detector to account for heel effects.

A starting x-ray image of an observed sample containing materials resembling the trainmen materials was taken and down sampled, the down sampling increasing computational efficiency but not being essential.

A first estimate of the matters in the sample was made. The median material and thickness from the database was use, which was 5 cm thickness of material comprised 50% of PMMA and 50% of aluminium.

Steps 1 to 4a described above were repeated until Z–S–D<threshold.

Figure 7:
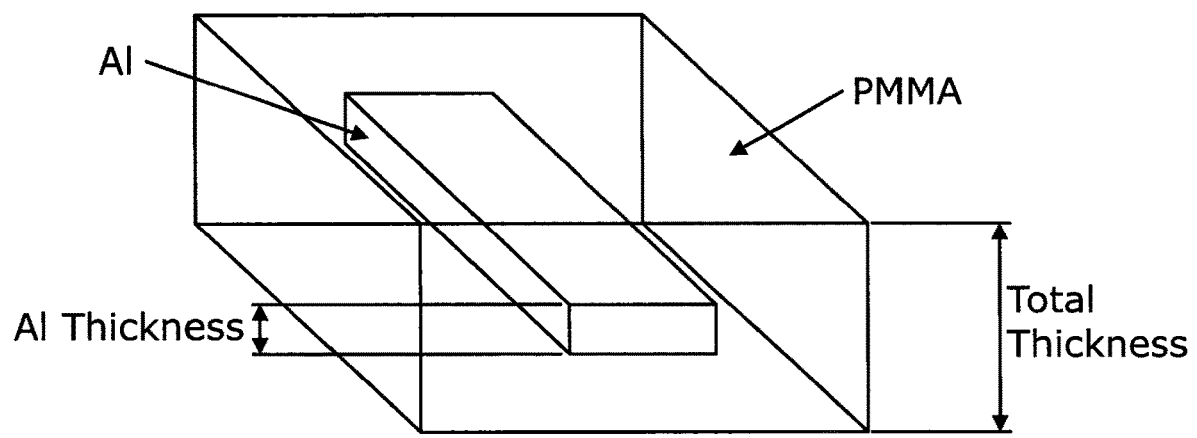
FIG. 7 is an illustration of the phantom used in Example 1.

FIG. 7 shows an image of the PMMA/Al phantom which has a total thickness of 7.6 cm and an aluminium insert which is 1.36 cm thick.

Figure 8:
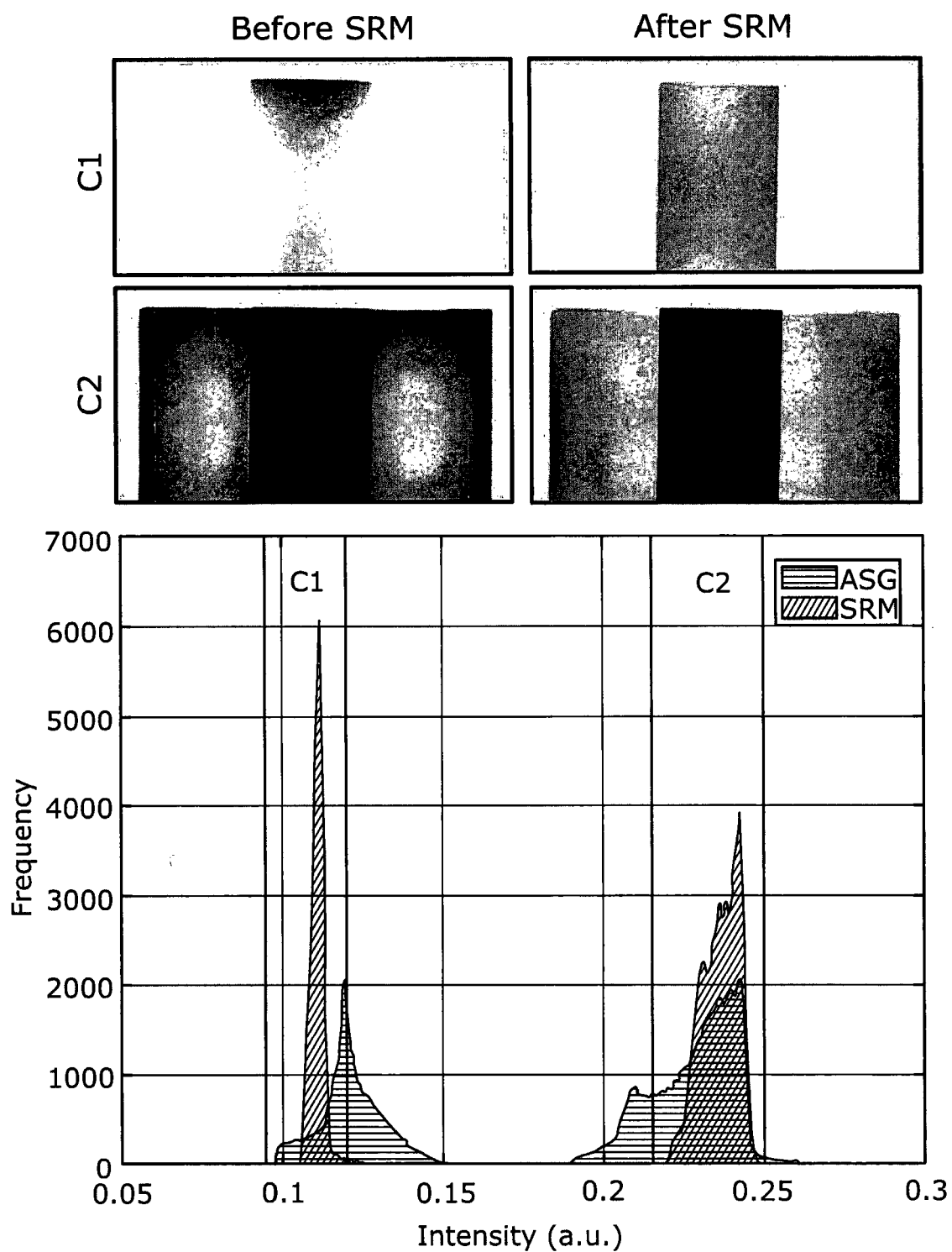
FIG. 8 illustrates x-ray images and intensity histograms for an x-ray image of the phantom of FIG. 7 without scatter correction and with scatter correction.

An X-ray image, shown in FIG. 8 was taken of the phantom without an anti scatter grid present. The intensity histograms at the bottom of the figure highlight the distortion due to scatter. This results in broad, asymmetric peaks. The second image, after scatter correction, returns a flattened image with narrower and more symmetric distributions.

Windowing the contrast range on the two images to the ranges defined by C1 and C2 shows the improvement in the image after the scatter reduction method of the invention has been applied. The resulting image is a much closer representation of the underlying sample and can be contrast windowed much more effectively.

Figure 9:
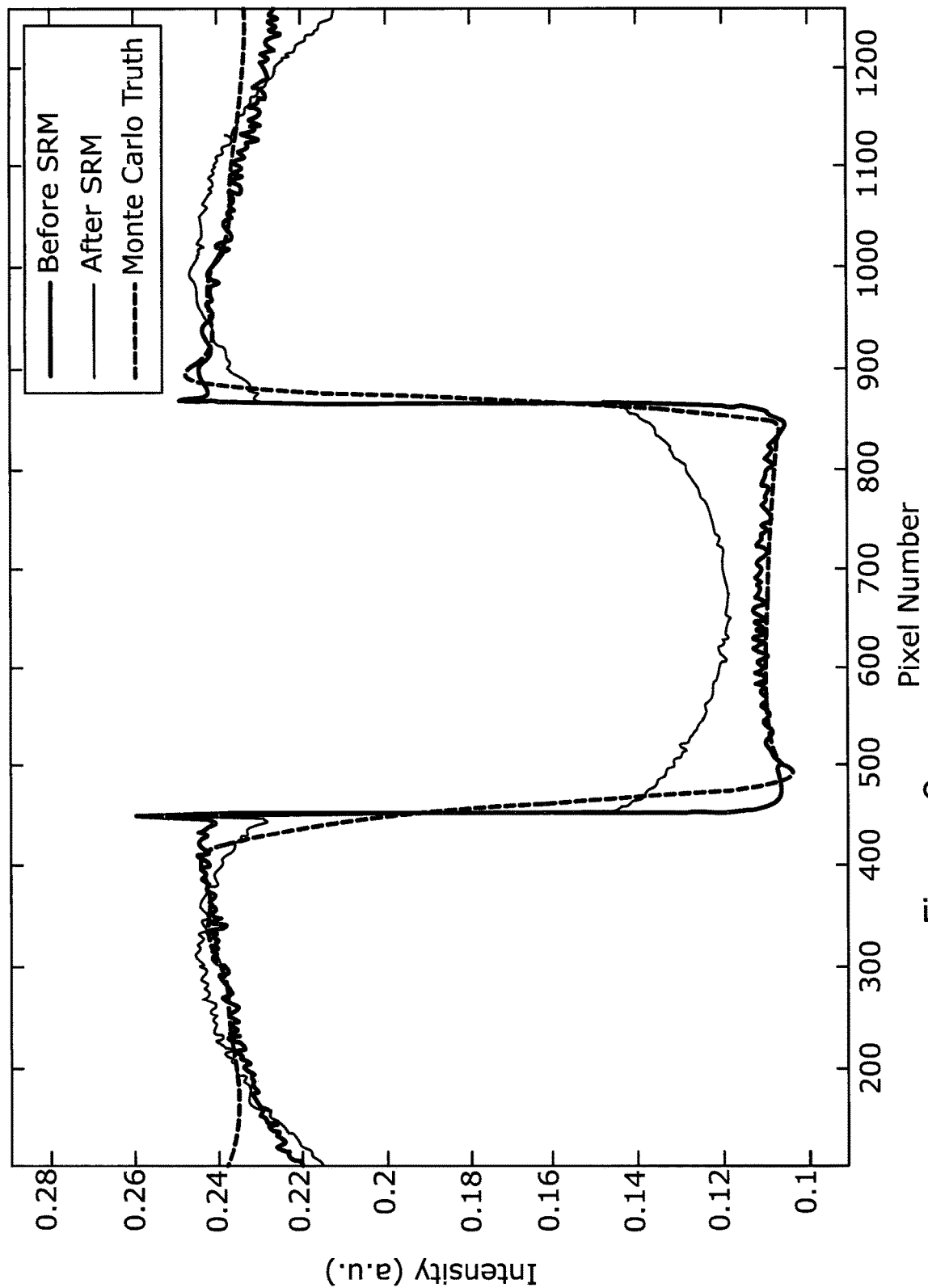
FIG. 9 illustrates line profiles from the x-ray images of FIG. 8.

Using a simulation of the phantom and knowledge of the materials present, it is possible to determine from the Monte Carlo truth what a perfectly scatter corrected image would look like. This is shown in FIG. 9 and demonstrates that the scatter reduction method of the invention returns corrected images which are faithful to the limiting case of perfect scatter correction.

The scatter reduction method of the invention relies on the determination of materials information in order to predict and correct scatter. As such the final converged solution produces both a corrected X-ray image and a map of material composition and thickness. The composition and thickness returned by the algorithm is within a few percent of the true values.

Example 2

Figure 10A:
FIGS. 10a and 10b illustrate x-ray images of the neck of a femur after scatter correction with the method of the invention and with an anti-scatter grid respectively.
Figure 10B:

The images shown in FIGS. 10a and 10b are of a neck of femur after scatter correction according to the method of the invention (FIG. 10a) and with an anti-scatter grid for comparison (FIG. 10b). These images were taken on a GE VMX Plus mobile X-ray system with a Rayence 1417 CsI detector.

The images in FIGS. 10a and 10b were taken at equivalent beam settings of 6.4 mAs and 75 kV and a source to detector distance of 115 cm. The image of FIG. 10a does not suffer from the absorption losses associated with an anti scatter grid, meaning that the dose at the detector is significantly higher in FIG. 10a even though the dose to the patient is the same. Comparing the signal to noise ratio (SNR) across the entire image shows the benefit of using the scatter reduction method of the invention over an anti scatter grid. Note, the image of FIG. 10a did not include the adding back of scatter radiation as pseudo direct radiation, which would improve the image still further.

Figure 11:
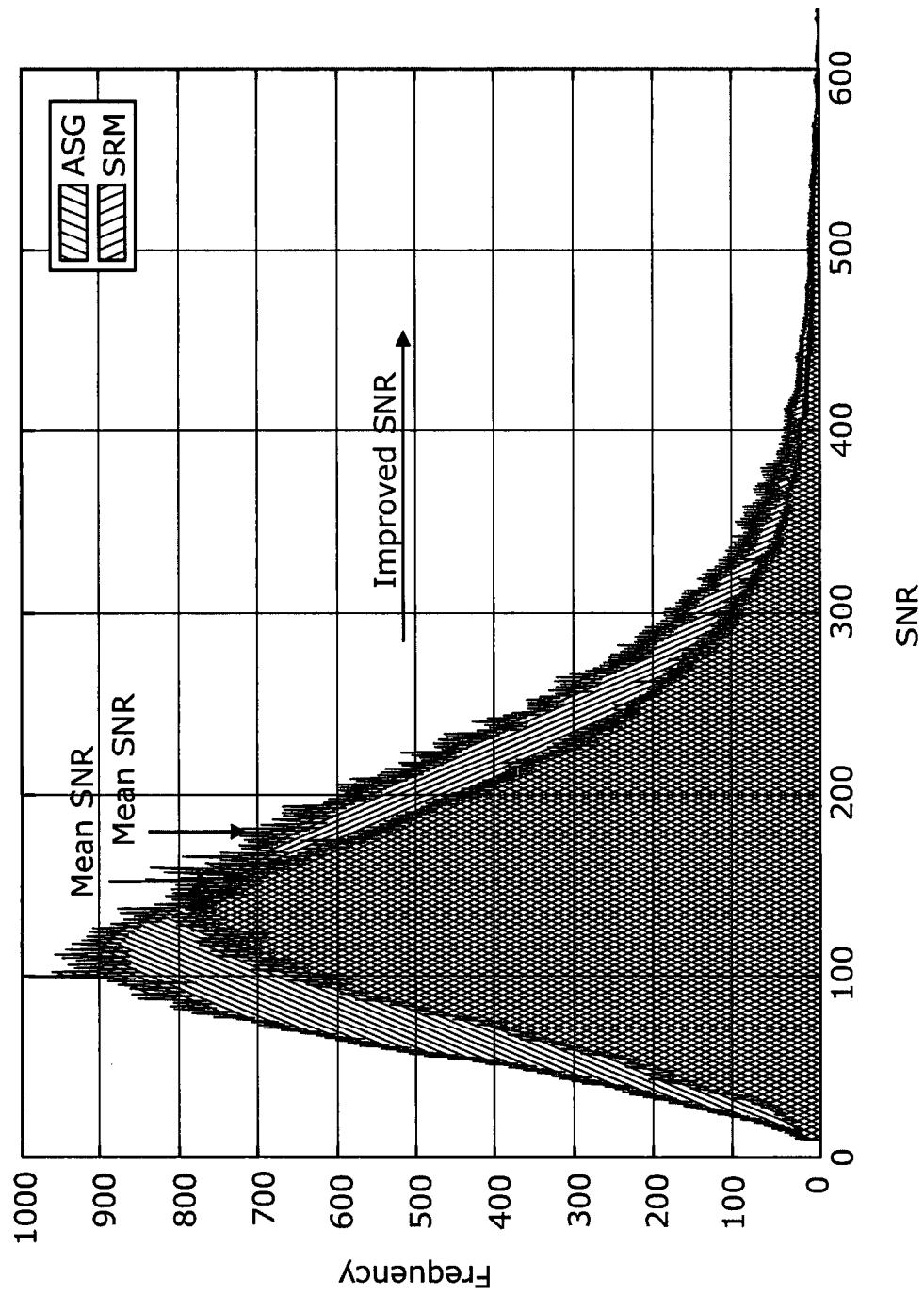
FIG. 11 shows histograms corresponding to the images of FIGS. 10a and 10b showing the difference in image quality between the image corrected for scatter with the method of the invention and the image corrected for scatter with an anti-scatter grid.

FIG. 11 shows a histogram of the SNR across the two images in FIGS. 10a and 10b. The scatter reduction method of the invention shows an improvement in SNR across the entire image when compared to an image taken with an anti-scatter grid present. This improvement relates to the higher detector dose from the removal of the anti-scatter grid, combined with a reduction of image artefacts associated with the lead vanes within the grid.

A summary of the improvements from over an ASG is shown in Table 1.

Detector Mean SNR Mode SNR

TABLE 1

Summry of detector dose and SNR improvements relative to using an ASG.

|  | Detector Dose (μGy) | Mean SNR | Mode SNR |
|---|---|---|---|
| SRM | 1.27 | 180.9 | 96.4 |
| ASG | 0.2 | 155.3 | 79.3 |
| Improvement Factor | x6.35 | x1.16 | x1.22 |

The improvement in SNR can be exploited to either increase the diagnostic quality of images or to lower the patient dose. We estimate that using the scatter reduction method of the invention it would be possible to reduce patient dose by around a factor of 2 whilst still returning the same image quality.

The dose or SNR improvements combined with materials information results in a method which makes much greater use of the available X-rays than a system which uses an anti scatter grid.

The invention claimed is:

1. An x-ray imaging method comprising the steps of:
  i. providing a set of at least one training material, the set comprising different materials and/or different thicknesses of the or each material;
  ii. obtaining observed x-ray images of the at least one training material with a pixellated detector;
  iii. building a database in a simulator of simulated scatter kernels for variable parameters within the simulator for each of the at least one training material;
  iv. comparing parameters of the observed x-ray images and parameters of images created by the simulator and identifying input parameters to the simulator which give rise to a transfer function between the images created by the simulator and the observed x-ray images which is independent of sample type and thickness;
  v. generating the transfer function;
  vi. obtaining an observed x-ray image with the pixellated detector of a sample that contains at least one material resembling the at least one training material;
  vii. making an initial estimate of the material type and/or thickness contained in the sample;
  viii. performing a ray path trace on the sample as if the material and thickness of the sample corresponds to the estimate of step vii from each of a plurality of spatially separated points on the sample to each pixel of the detector;
  ix. obtaining a scatter kernel from a scatter kernel database corresponding to a spread function of each ray path trace;
  x. sum the scatter for each scatter kernel to provide a whole image scatter estimate;
  xi. predict the direct radiation for each scatter kernel;
  xii. apply the transfer function to the scatter estimate and the direct radiation or the inverse of the transfer function to the observed x-ray image;
  xiii. perform the calculation Z−S−D<threshold where Z is the observed x-ray image, S is the scatter radiation estimate post application of the transfer function and D is the direct radiation post application of the transfer function, or where Z is the observed x-ray image post application of the inverse of the transfer function, S is the scatter estimate and D is the direct radiation;
  xiv. if Z−S−D<threshold subtract S from Z to provide scatter free data and/or a scatter free image.

2. The x-ray imaging method according to claim 1, wherein the database of scatter kernels built in step iii is built for a sub-set of all variable parameters within the simulator for each of the at least one training material.

3. The x-ray imaging method according to claim 1, wherein the variable parameters in step iii are selected from the group comprising: kV, filtration and sample position.

4. The x-ray imaging method according to claim 1, wherein the step of obtaining an x-ray image with a pixellated detector comprises recording intensity values at each pixel of the detector.

5. The x-ray imaging method according to claim 1, wherein the initial estimate (step vii) is based on one of: the intensity values associated with individual pixels or groups of pixels from step vi; a statistical value related to the materials and material thicknesses contained in the database of training materials; a random guess; material type and thickness information from another system.

6. The x-ray imaging method according to claim 1, wherein obtaining a scatter kernel database comprises one of: emulating a scatter kernel from scatter kernels in the scatter kernel database; interpolating between scatter kernels from the scatter kernel database; and selecting a scatter kernel.

7. The x-ray imaging method according to claim 6, wherein the scatter kernel database is sparsely populated and scatter kernels are emulated from or interpolated between points in the sparsely populated scatter kernel database.

8. The x-ray imaging method according to claim 1, including the further step of adding back to the scatter free data, scatter radiation as if that scatter radiation had been direct radiation and providing enhanced scatter free data and/or an enhanced scatter free image.

9. The x-ray imaging method according to claim 1, wherein scatter free data comprises material type and/or material thickness information.

10. An x-ray imaging apparatus comprising an x-ray source, a pixellated x-ray detector, a simulator and a data processor, the data processor configured to:
  obtain an observed x-ray image with the pixellated detector of a sample that contains at least one material;
  make an initial estimate of the material type and/or thickness contained in the sample;
  perform a ray path trace on the sample as if the material and thickness of the sample corresponds to the initial estimate from each of a plurality of spatially separated points on the sample to each pixel of the detector;
  obtain a scatter kernel from a scatter kernel database corresponding to a spread function of each ray path trace;
  sum the scatter for each scatter kernel to provide a whole image scatter estimate;
  predict the direct radiation for each scatter kernel;
  apply a transfer function to the scatter estimate and the direct radiation or the inverse of the transfer function to the observed x-ray image;
  perform the calculation Z−S−D<threshold where Z is the observed x-ray image, S is the scatter estimate post application of the transfer function and D is the direct radiation post application of the transfer function, or where Z is the observed x-ray image post application of the inverse of the transfer function, S is the scatter estimate and D is the direct radiation;

if Z−S−D<threshold, subtract S from Z to provide scatter free data and/or a scatter free image.

11. The x-ray imaging system comprising x-ray imaging apparatus according to claim 10 and a set of at least one training material, the set comprising different materials and/or different thicknesses of the or each material.

\* \* \* \* \*